US007265352B2

(12) United States Patent
Muehllehner et al.

(10) Patent No.: US 7,265,352 B2
(45) Date of Patent: Sep. 4, 2007

(54) REAL-TIME LIST MODE RECONSTRUCTION

(75) Inventors: Gerd Muehllehner, Wayne, PA (US); Michael J. Parma, Philadelphia, PA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/467,658

(22) Filed: Aug. 28, 2006

(65) Prior Publication Data

US 2006/0284095 A1 Dec. 21, 2006

Related U.S. Application Data

(63) Continuation of application No. PCT/IB2005/054166, filed on Dec. 9, 2005.

(60) Provisional application No. 60/638,915, filed on Dec. 22, 2004.

(51) Int. Cl.
*G01T 1/161* (2006.01)
*G01T 1/164* (2006.01)
*G01T 1/166* (2006.01)

(52) U.S. Cl. .................... 250/363.02; 250/363.03; 250/363.04

(58) Field of Classification Search .......... 250/363.02, 250/363.03, 363.04
See application file for complete search history.

(56) References Cited

U.S. PATENT DOCUMENTS

| 4,559,597 | A | * | 12/1985 | Mullani ................. 600/407 |
| 4,575,868 | A | * | 3/1986 | Ueda et al. ............... 378/4 |
| 4,931,968 | A | * | 6/1990 | Hirose .................. 250/363.07 |
| 4,980,552 | A | * | 12/1990 | Cho et al. ............. 250/363.03 |
| 5,204,943 | A | * | 4/1993 | Watanabe et al. ........... 345/418 |
| 5,241,181 | A | * | 8/1993 | Mertens et al. ........ 250/363.03 |
| 5,337,231 | A | * | 8/1994 | Nowak et al. .............. 600/425 |

(Continued)

FOREIGN PATENT DOCUMENTS

EP  1 288 679 A1  3/2003

(Continued)

OTHER PUBLICATIONS

Dahlbom et al., "Implementation of True Continuous Bed Motion in 2-D and 3-D Whole-Body PET Scanning." IEEE Transactions on Nuclear Science, vol. 48, No. 4 (Aug. 2001), pp. 1465-1469.*

*Primary Examiner*—David Porta
*Assistant Examiner*—Mindy Vu

(57) ABSTRACT

In positron emission tomography, a nuclear medicine scanner is utilized to detect γ-ray events resulting from positron annihilation events. Molecules with known behaviors are tagged with radioactive isotopes which decay into γ-ray pairs which are detected coincidentally, i.e. in a near-simultaneous fashion, by radiation detectors. A temporal recorder and a subject support monitor indicate the time and position of the subject when the coincident γ-rays were detected. A storage buffer collects γ-ray detection times and locations along with support positions. Every $\frac{1}{100}^{th}$-$\frac{1}{10}^{th}$ second, a batch of data collected in the buffer is reconstructed into overlapping portions of an image memory as the support moves continuously through the scanner.

22 Claims, 3 Drawing Sheets

U.S. PATENT DOCUMENTS

| | | |
|---|---|---|
| 5,431,161 A | 7/1995 | Ryals et al. |
| 6,194,726 B1 * | 2/2001 | Pi et al. .................. 250/363.1 |
| 6,410,920 B1 | 6/2002 | Shao et al. |
| 6,541,763 B2 | 4/2003 | Lingren et al. |
| 6,631,284 B2 | 10/2003 | Nutt et al. |
| 6,915,004 B2 * | 7/2005 | Newport et al. ............ 382/131 |
| 2003/0161521 A1 | 8/2003 | Newport et al. |
| 2004/0069951 A1 | 4/2004 | Jones et al. |
| 2004/0084624 A1 | 5/2004 | Meng et al. |

FOREIGN PATENT DOCUMENTS

| | | |
|---|---|---|
| JP | 63115079 A | 5/1988 |
| JP | 09005441 A | 1/1997 |
| WO | WO 97/21113 A2 | 6/1997 |
| WO | WO 03/086170 A2 | 10/2003 |

\* cited by examiner

REAL-TIME LIST MODE RECONSTRUCTION

CROSS REFERENCE TO RELATED APPLICATIONS

This application is a Continuation of PCT application number PCT/IB2005/054166 filed Dec. 9, 2005 which claims the benefit of U.S. provisional application Ser. No. 60/638,915 filed Dec. 22, 2004, both of which are incorporated herein by reference.

BACKGROUND OF THE INVENTION

The present invention relates to the field of medical imaging. It finds particular application to the acquisition of time of flight (TOF) positron emission tomography (PET) scans, and will be described with particular reference thereto. The invention is also applicable to single photon emission computed tomography (SPECT), and PET as well as other imaging modalities.

Typically, in nuclear imaging, a subject is imaged in axial slices that combine to form a 3D representation of a region of interest. This region could be localized, such as the brain or heart, but it is also typical to perform full body PET scans. Some PET scanners utilize a step and shoot method of data collection, typically utilizing a data acquisition window of about 10 cm wide. Typically, data is collected in a given bed position in frame mode and are transferred so that they are available for reconstruction only after all of the events for a given bed position have been collected. Some Pet scanners move the bed continuously and collect the events in list mode, the events stored first in a buffer and then, after one or several buffers are full, are stored to a disc. Reconstruction then begins after all the data collection has been completed. Specifically, the data is sorted to find substantially redundant rays which are summed and reconstructed in a common operation.

Both of the present methods cause a delay before the reconstruction can begin. Resultantly, images are completed after they would have been had reconstruction began soon after data collection. Reconstruction does not begin until at least after the first region has left the data acquisition window in the step and shoot mode. When the data is reconstructed in sections as separate images, interface discontinuities or artifacts commonly occur. All the data has to be collected in a continuous bed movement scan before reconstruction can start as it is currently implemented. As it stands currently, there is always some delay between the start of data acquisition and the start of reconstruction.

The present application contemplates a new and improved nuclear imaging apparatus and accompanying method that overcome the above-referenced problems and others.

SUMMARY OF THE INVENTION

In accordance with one aspect of the present invention, a nuclear emission apparatus is presented. A subject support surface supports a subject injected with a radiopharmaceutical, which radiopharmaceutical emits γ-rays. Selected anatomy of the subject is moved through a detection region. A subject support monitor monitors a position of the subject support surface during a data acquisition process. A γ-ray detector assembly for detects emitted γ-rays and converts them into electrical signals indicative of at least detection location. A storage buffer temporarily stores batches of the electrical signals and corresponding subject support positions. A reconstruction processor reconstructs one batch of signals from the storage buffer as the storage buffer stores a next batch of electrical signals and corresponding support positions into an image representation.

In accordance with another aspect of the present invention, a method of nuclear emission is presented. A subject is supported and injected with a radiopharmaceutical that emits γ-rays. Selected anatomy of the subject is moved through a detection region. The position of the subject is monitored during a data acquisition process. Emitted γ-rays are detected and electrical signals indicative of γ-ray detection locations are generated. A time of reception of a first γ-ray is recorded and a delay time between reception of the simultaneously emitted γ-rays is also recorded. The electrical signals with corresponding subject support positions are temporarily stored in batches. Received pairs of γ-rays are analyzed to determine if they originated from valid annihilation events. One batch of the temporarily stored electrical signals is withdrawn and reconstructed as a next batch of the electrical signals with corresponding subject support positions is stored.

One advantage of the present invention resides in faster image reconstruction.

Another advantage resides in improved subject throughput.

Another advantage resides in images available for review while the subject is still on the premises.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figure 1:
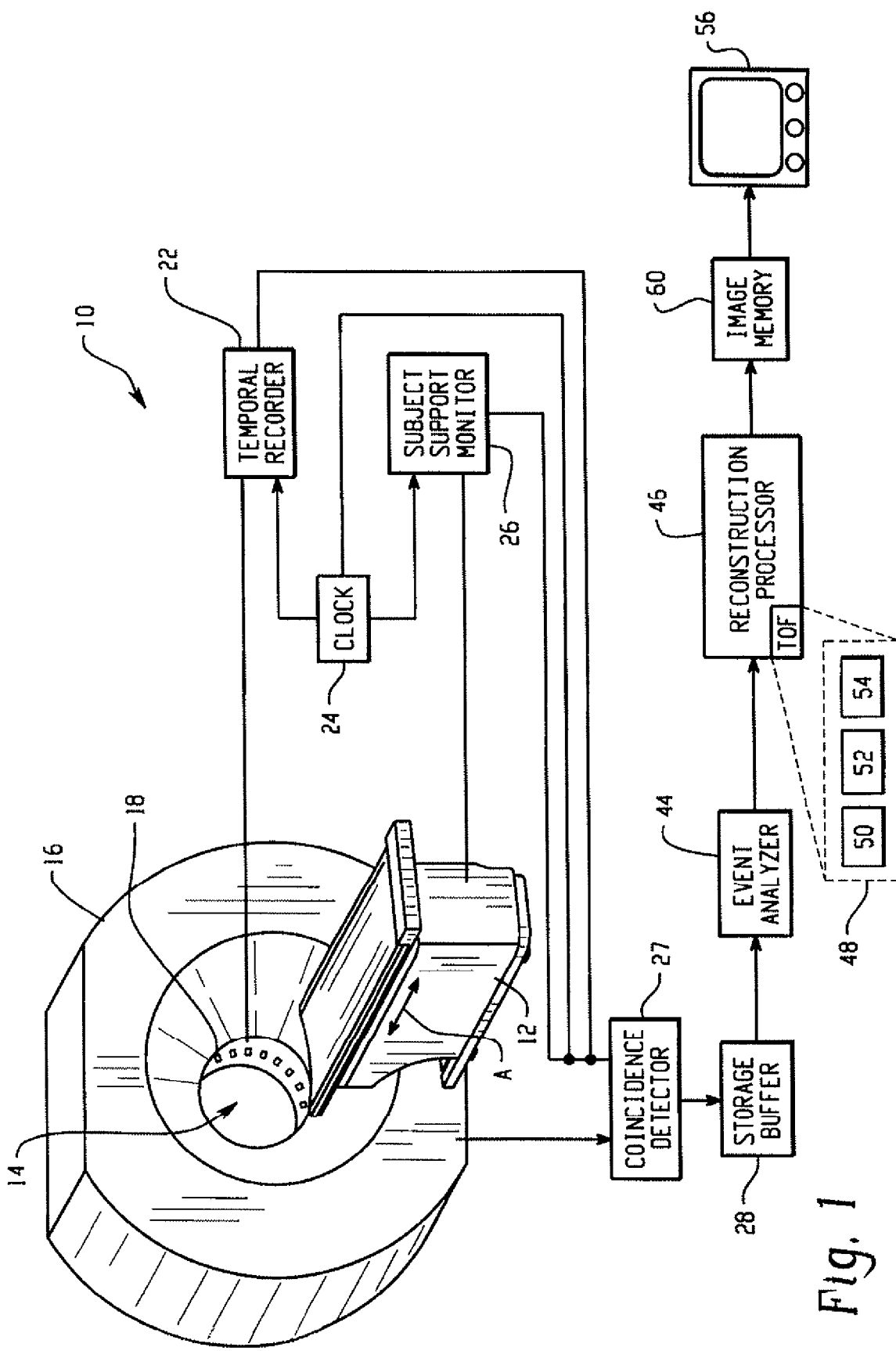
FIG. 1 is a diagrammatic illustration of a nuclear medicine scanner in accordance with the present application.

With reference to FIG. 1, a preferred embodiment of a nuclear medicine scanner 10 is shown. Prior to a scan, a subject is placed on a subject support surface 12. The subject support surface of moves along its longitudinal axis A, into and out of a bore 14 of a gantry 16 of the scanner 10. The bore of a PET scanner is lined with a cylinder of radiation detectors 18. Optionally, the detectors include a plurality of detector heads. In either ease, the detectors 18 are disposed around and along the subject receiving bore 14 to receive nearly concurrently incident γ-rays. Typically, incident γ-rays strike the detectors 18 which preferably include an array of scintillation crystals and photodetectors, although solid state, Anger-type, and other detectors are contemplated. The scintillation crystals emit small bursts of visible light when they are struck with γ-rays, and the visible light is detected by the photodetectors and converted into electrical signals. Solid state detectors, that convert the incident γ-rays directly into electronic signals, eliminate the step of conversion into equivalent light signals.

The subject is injected with a radiopharmaceutical. The radiopharmaceutical is a specially engineered radioactive isotope that is created for the purpose of positron emission. Fluorine is an exemplary isotope created for PET imaging, but other isotopes are certainly contemplated. To create the radioactive fluorine, single protons (hydrogen) are accelerated toward target oxygen atoms. If the protons strike the oxygen nuclei with sufficient energy, the protons bond with the nuclei displacing single neutrons. The chemical reaction proceeds as follows:

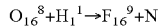

The resulting fluorine is unstable, having a half-life of 110 minutes, leaving relatively narrow windows for transport or other delays. Many PET scanning facilities have on-site labs with particle accelerators, but smaller scanning operations transport the radiopharmaceutical in from nearby dedicated facilities.

Typically, the oxygen atoms used are a part of a larger molecule, one with known interactions with the human body, e.g. glucose. It is known that glucose, as a source of energy for cells, tends to end up in areas of the body with high metabolic rates. This is particularly useful for imaging the heart and brain. The heart expends more energy per unit volume than any other area in the body, and as brain cells are incapable of storing energy, they require the raw glucose to metabolize on-demand. Glucose also tends to end up in malignant tumors, as cancer cells have abnormally high metabolic rates. So by "tagging" these glucose molecules with radioactive fluorine, the fluorine later decaying when the glucose has settled in an area of interest, the PET scanner can construct an image according to the glucose concentration. Beneficially, substitution of the one fluorine atom in a glucose molecule does not substantially affect interaction with the body. Eventually the tagged glucose settles in the areas with the highest metabolization. Once there, some of the fluorine tags decay while the subject is in the imaging region.

Fluorine$_{19}$ is the most stable form of elemental fluorine. Fluorine$_{16}$ has too few neutrons in its nucleus, rendering it unstable. As a general rule, elements tend to return to the most stable state possible. The most energy efficient way for fluorine$_{16}$ to return to stability is to return to oxygen$_{16}$ which is done by converting one of its protons into a neutron. The physical doctrine of conservation of charge dictates that charge of a system must remain balanced, so when the nucleus becomes less positive (by losing a proton) the surrounding area becomes equally more positive. The nucleus does this by releasing a positron. A positron is the anti-matter equivalent to an electron. It has the same mass, with an equal but opposite charge.

After the positron is released from the unstable fluorine nucleus, it propagates until it contacts an electron, causing an annihilation reaction to occur. An annihilation reaction occurs generally when matter meets its anti-matter counterpart, in this case, an electron and a positron. Resultantly, all mass in the reaction is converted totally into energy, particularly two 511 eV γ-rays that propagate in opposite directions, to conserve momentum of the system. That is, the two γ-rays travel in opposite directions along a common ray.

Figure 2:
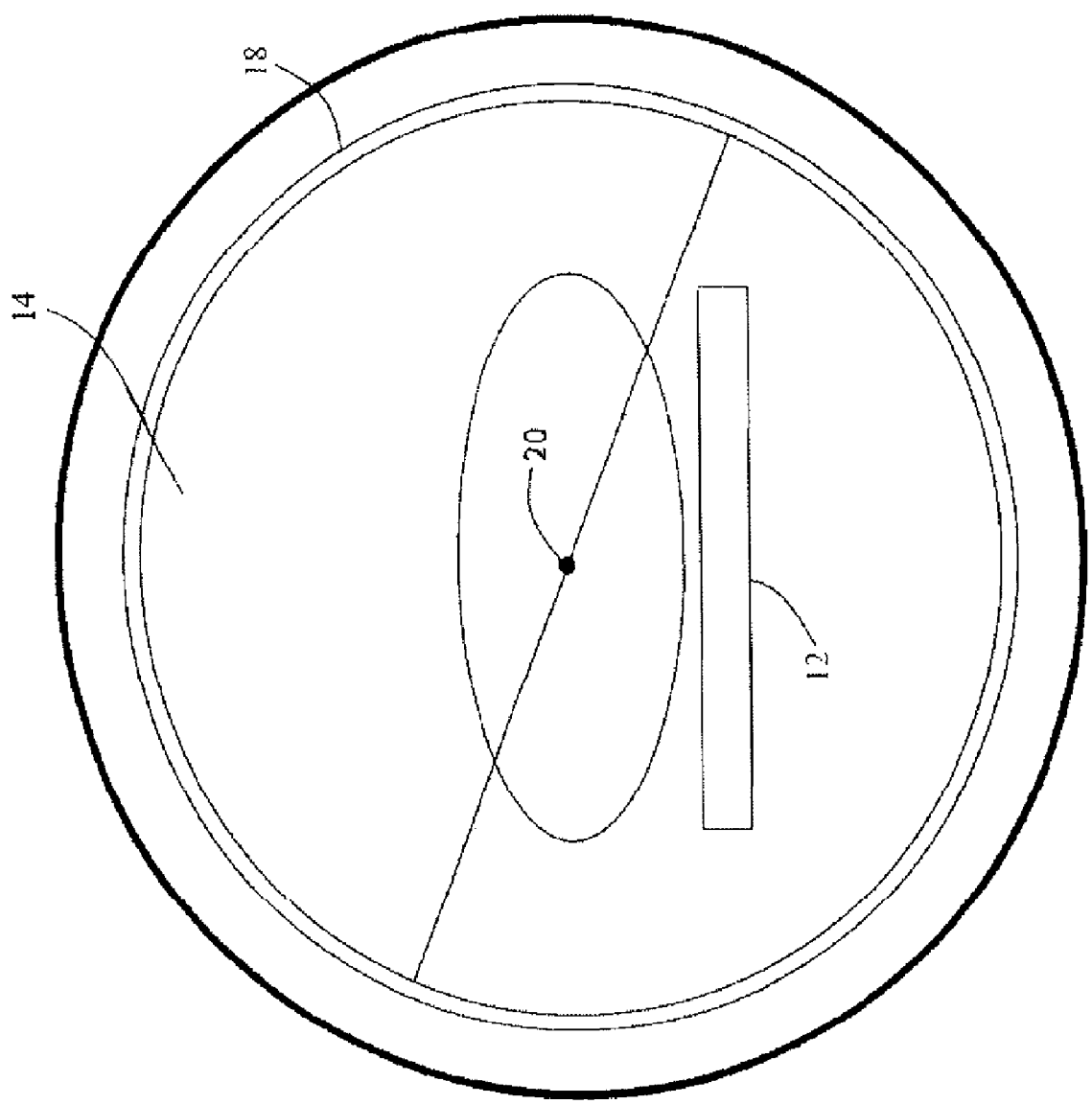
FIG. 2 is an axial view down a bore of the scanner of FIG. 1 showing a valid annihilation event.

When the annihilation events occur within the bore 14 of the scanner, it will be detected as a valid annihilation event if both γ-rays strike detectors substantially simultaneously. With reference to FIG. 2, an annihilation event 20 releases equal energy and oppositely propagating γ-rays. Both γ-rays are detected on opposite sides of the bore. In order to validate the event, the time that the first γ-ray is detected is recorded by a temporal recorder 22 that receives timing information from an independent system clock 24. A subject support monitor 26 also records the bed position at the time of the event. If a second γ-ray is received within an acceptable time window of the first γ-ray, then a coincidence detector 27 passes the pair on to a storage buffer 28 for further analysis. If a second γ-ray is not received in close enough temporal proximity to the first, the first γ-ray is discarded as unpaired, the γ-rays are assumed to be from different annihilation events, i.e. an invalid annihilation event. Pairs of γ-rays are localized in three dimensions before reconstruction. With the bed position from the subject support monitor 26 the system 10 is able to commence reconstruction as soon as the events are validated without having to wait on further events to be collected by the system 10.

Figure 3:
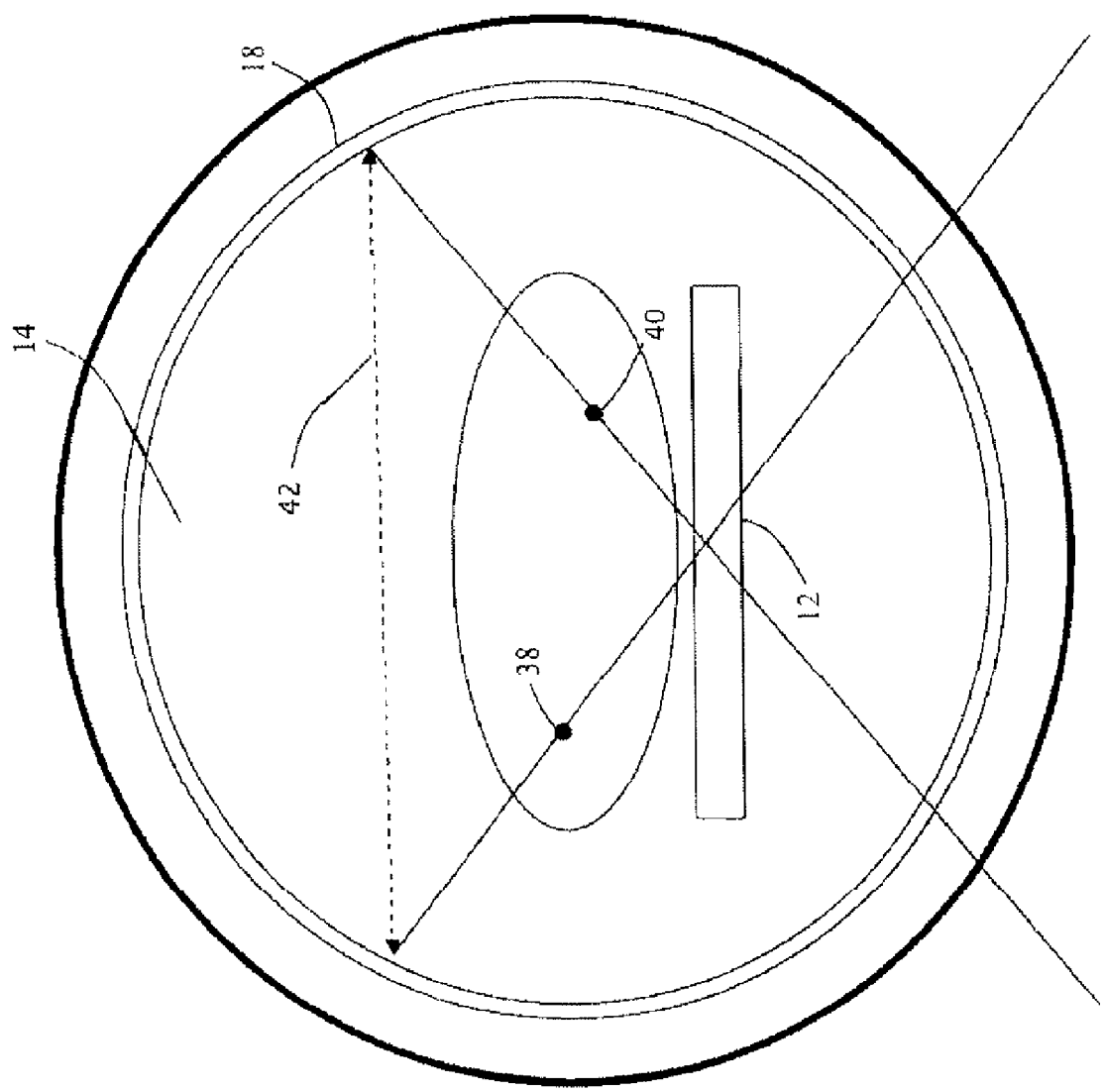
FIG. 3 is a view down the bore of the scanner of FIG. 1 showing an invalid event.

In some cases, as shown in FIG. 3, nearly concurrent annihilation events, within a few picoseconds of each other, can be discarded because the resultant ray represents an impossible trajectory, such as a path that does not intersect the subject. Events 38 and 40 generate pairs of γ-rays, only half of which hit a detector. The other two γ-rays are not detected for one of various reasons such as their trajectory exits the end of the bore 14, they are absorbed by bone or other dense tissue, they are scattered, or the like. The two rays which survive appear to combine to form a ray 42, but at a trajectory that does not intersect the subject. An event analyzer 44 analyzes the trajectory information of the detected γ-ray pairs to invalidate those with impossible trajectories.

Further, the event analyzer 44 receives bed position information from the subject support monitor 26 for analyzing whether annihilation events are valid or not. In scatter radiation situations, it may appear that the annihilation events originated outside the gantry 16 while these γ-rays may have originated from the same annihilation event, their energies or trajectories may have been skewed, rendering them inapplicable to study.

Another calculation that the event analyzer 44 makes to eliminate apparently invalid annihilation events is based on a time of flight (TOF) calculation. The event analyzer 44 takes the time of incidence of the first γ-ray and compares it to the time of incidence of the second γ-ray and compares them to see if one or both of them was traveling faster or slower than the speed of light, within acceptable tolerances, naturally rendering them as false events.

After the event analyzer 44 has exhausted its methods to eliminate invalid annihilation events, a reconstruction processor 46 reconstructs the valid events into an image representation of the subject. In previous processing, the γ-rays have already been localized to a single ray in space, originating from a point where the annihilation took place and propagating oppositely along the same ray. The reconstruction processor includes a TOF routine 48 which uses the TOF information to further localize the origin of the γ-rays along the trajectory ray. For example, with a clock speed of 10 GHz, TOF information can localize the annihilation event to within three centimeters along the ray. As system clock speeds improve, localization along the ray will become more precise, helping to localize the event down to millimeters, and perhaps obviate the need to apply a separate backprojection algorithm. The reconstruction processor 46 applies a reconstruction algorithm which reconstructs the ray segments into an image of the anatomical structures of interest, as previously discussed, e.g. the regions with the highest metabolism and highest glucose uptake.

The time of flight processor includes a routine 50 for determining the difference between the receipt times for each γ-ray of the pair. A routine 52 determines the center point of the corresponding ray. From the difference in receipt times and the known speed of γ-rays, a routine 54 determines how far from center and in which direction along the ray the annihilation event occurred. Ideally, the location would be a point. In practice, the γ-ray travel speeds are so high relative to the distances traveled and the accuracy of the time measurements, that the event often can only be localized to a segment of the ray.

If the event location is determined to within 1 voxel, the corresponding voxel of the image memory is indexed 1 count. If the ray segment intersects two or more voxels, other reconstructions are used. As one example, the segment is filtered, e.g. with a Gaussian of unit area and the length of the segment. The integration of the portion of the filtered segment (typically a number less than 1) which traverses each voxel is added to that voxel. As another option, the segment is filtered and backprojected along its length.

As the first sets of data roll into the storage buffer 28 the system 10 has all the information it needs to begin the event analysis and reconstruction processes. As events are recorded on the order of about 100,000 per second, it is contemplated that the buffer 28 stores 1,000 to 10,000 events before passing them on for individual analysis and reconstruction (every $\frac{1}{100}$-$\frac{1}{10}$ of a second). Optionally, the buffer 28 has two sections which are toggled. That is, one section stores new data in the other section while data is read out of the other for reconstruction. The two sections reverse when the reconstruction of one of the sections is completed. With the detection times and detector locations in the patient frame of reference of each event from the temporal recorder 22 and the position of the subject support from the subject support monitor 26, the event analyzer 44 can begin sorting valid events from invalid events. The TOF processor 48 identifies the ray segments. The reconstruction processor 46 starts reconstructing an image representation without waiting for the scan to complete or even a portion of the scan to complete. The subject support 12 does not have to move. Waiting for such a (comparatively) small amount of information also makes continuous bed motion much more practicable.

A display monitor 56 displays the reconstructed portions of the subject's anatomy. The monitor 56 preferably displays the portions of anatomy as the reconstruction process is ongoing. With reconstruction commencing during scanning, at least a preliminary image will be available for the subject to view before they leave the imaging suite.

Alternatively, the event analyzer 44 and/or the TOF processor 48 can be located between the temporal recorder 22 and the storage buffer 28 such that the storage buffer stores only the valid ray segments. The present system, without the TOF processor, is also suitable for SPECT, conventional PET and analogous scanners.

The reconstruction processor 48 reconstructs the data into an image memory 60. Particularly for whole body scans, the image memory corresponds to an elongated portion or all of the subject. Yet only a portion of the subject is in the detection region. As the patient moves continuously through the detection region, the portion of the image memory into which the data is reconstructed advances accordingly. Because each reconstructed batch of data is collected over $\frac{1}{100}^{th}$ to $\frac{1}{10}^{th}$ of a second and it takes several minutes, e.g. 5-30 minutes, to move the patient the full scan distance, each batch of data is reconstructed into mostly the same region as the preceding batch.

Displayed images of the region of the subject which have passed through and excited the detection region are fully sampled and of the best resolution. Images of the subject region near the leading edge of the detection region are sparsely sampled and of low resolution. However, as addition batches are reconstructed, the displayed image gradually improves in resolution reaching its maximum resolution as the displayed region exits the detection region.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A nuclear emission apparatus comprising:
    a subject support surface for supporting a subject injected with a radiopharmaceutical, which radiopharmaceutical emits γ-rays and moving selected anatomy of the subject through a detection region;
    a subject support monitor for monitoring a position of the subject support surface during a data acquisition process;
    a γ-ray detector assembly for detecting emitted γ-rays and converting them into electrical signals indicative of at least detection location;
    a storage buffer that temporarily stores batches of the electrical signals in list mode and corresponding subject support positions;
    a reconstruction processor that reconstructs one batch of signals from the storage buffer into an image representation as the storage buffer stores a next batch of electrical signals and corresponding support positions; wherein the batches of signals and corresponding subject support positions are determined independently of the subject support position.

2. The apparatus as set forth in claim 1, wherein the detector assembly includes two or more detectors, wherein the detectors are positioned to receive simultaneously emitted γ-ray pairs, the from annihilation events and further including:
    a temporal recorder that records relative times of detection of the γ-rays;
    a coincidence detector for identifying corresponding pairs of γ-rays, the buffer storing the detection locations of the γ-rays of each detected pair.

3. The apparatus as set forth in claim 2, further including:
    a time of flight processor which determines from the detection locations and the relative detection times, a segment of a ray between the detection locations along which the annihilation event occurred, the reconstruction processor reconstructing the ray segments into the image representation.

4. The apparatus as set forth in claim 3, further including:
    an event analyzer that pre-processes received pairs of γ-ray detection locations and times to determine if they originated from valid annihilation events.

5. The apparatus as set forth in claim 4, wherein the event analyzer uses subject support position information and time of flight information to determine valid annihilation events.

6. The apparatus as set forth in claim 4, further including:
    a system clock that provides the temporal recorder, the subject support monitor, the storage buffer, and the event analyzer with an absolute system time standard for coordinating reconstruction of received γ-rays.

7. The apparatus as set forth in claim 1, wherein the reconstruction processor commences reconstruction substantially concurrently with the collection of data.

8. The apparatus as set forth in claim 1, wherein the storage buffer includes two sections that toggle alternately such that one receives newly collected data as the stored data in the other section is reconstructed.

9. The apparatus as set forth in claim 1, wherein each batch of the storage buffer is collected over a period of 1/100th to 1/10th of a second.

10. A method of nuclear emission imaging comprising:

supporting a subject injected with a radiopharmaceutical that emits γ-rays on a subject support and moving selected anatomy of the subject through a detection region;

monitoring the position of the subject during a data acquisition process;

detecting emitted γ-rays and generating electrical signals indicative of γ-ray detection locations at which pairs of γ-rays are coincidently detected;

recording relative times of detection of each pair of coincident γ-rays;

temporarily storing in list mode the electrical signals indicative of the detection locations with corresponding subject support positions and relative detection times in batches;

analyzing the pairs of coincident γ-rays to determine if they originated from valid annihilation events;

withdrawing and reconstructing one batch of the temporarily stored electrical signals as a next batch of the electrical signals with corresponding subject support positions is stored; wherein the batches of signals and corresponding subject support positions are determined independently of the subject support position.

11. The method as set forth in claim 10, wherein each batch is accumulated for a period of 1/100th to 1/10th of a second.

12. The method as set forth in claim 10, further including:

positioning detectors to receive coincidentally emitted γ-ray pairs from annihilation events;

recording relative times of reception of the γ-rays;

identifying corresponding pairs of coincident γ-rays and storing the detection locations of the γ-rays of each detected coincident pair.

13. The method as set forth in claim 12, further including:

determining a ray between the detection locations;

from the relative detection times, determining of the coincident pairs of γ-rays a segment of the ray along which the annihilation event occurred; and reconstructing the ray segments into an image representation.

14. The method as set forth in claim 13, further including:

pre-processing the pairs of coincident γ-rays to determine if they originated from valid annihilation events.

15. The method as set forth in claim 10, further including:

commencing reconstruction substantially concurrently with the collection of data.

16. The method as set forth in claim 10, further including:

receiving newly collected data as stored data is reconstructed.

17. The method as set forth in claim 10, wherein γ-rays are detected at a rate of at least 100,000 per second and each batch stores about 1000 to 10,000 γ-ray pairs.

18. The method as set for the in claim 10, wherein the subject support moves continuously through a γ-ray detection zone over a period of several minutes.

19. An imaging system comprising:

a subject support surface for supporting a subject injected with a radiopharmaceutical;

a subject support monitor for monitoring a position of a subject support surface during a data acquisition process;

a detector assembly for detecting emitted radiation;

an event analyzer that eliminates detected radiation prior to reconstruction, wherein the event analyzer eliminates detected radiation events based on event location outside a region of interest; and a reconstruction processor that reconstructs positionally independent batches of detected radiation events to form at least a portion of an image while subsequent batches of radiation are still being detected.

20. The imaging system of claim 19 wherein the event analyzer eliminates events during the acquisition process.

21. The imaging system of claim 19 further comprising a storage buffer for storing batches of detected radiation events, and wherein the reconstruction processor reconstructs one batch from the storage processor while another batch is being stored in the storage buffer.

22. The imaging system of claim 19, wherein the event analyzer eliminates detected radiation events based on both non-coincidence timing and event location outside the region of interest.

* * * * *